US010839947B2

(12) United States Patent
Barker et al.

(10) Patent No.: US 10,839,947 B2
(45) Date of Patent: *Nov. 17, 2020

(54) CLINICALLY RELEVANT MEDICAL CONCEPT CLUSTERING

(71) Applicant: International Business Machines Corporation, Armonk, NY (US)

(72) Inventors: Kenneth J. Barker, Mahopac, NY (US); Murthy V. Devarakonda, Peekskill, NY (US); Ching-Huei Tsou, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 895 days.

This patent is subject to a terminal disclaimer.

(21) Appl. No.: 14/988,787

(22) Filed: Jan. 6, 2016

(65) Prior Publication Data

US 2017/0193185 A1     Jul. 6, 2017

(51) Int. Cl.
*G16H 10/60*     (2018.01)
*G16H 50/70*     (2018.01)
*G06F 16/28*     (2019.01)
*G06F 16/33*     (2019.01)
*G06F 16/35*     (2019.01)

(52) U.S. Cl.
CPC .......... *G16H 10/60* (2018.01); *G06F 16/285* (2019.01); *G06F 16/334* (2019.01); *G06F 16/353* (2019.01); *G16H 50/70* (2018.01)

(58) Field of Classification Search
CPC ........ G16H 10/60; G16H 50/70; G06F 19/00; G06F 19/30; G06F 19/32; G06F 19/34; G06F 17/30598; G06F 17/30707; G06F 17/30675; G06Q 50/22; G06Q 50/24

USPC ........................................................ 705/3
See application file for complete search history.

(56) References Cited

U.S. PATENT DOCUMENTS

| | | | | |
|---|---|---|---|---|
| 6,629,097 B1 * | 9/2003 | Keith | .................. | G06F 16/9558 |
| 7,085,771 B2 * | 8/2006 | Chung | ................ | G06F 17/2785 |
| 7,194,471 B1 * | 3/2007 | Nagatsuka | ............ | G06F 16/355 |
| 7,469,246 B1 * | 12/2008 | Lamping | ............... | G06F 16/353 |
| 7,783,106 B2 * | 8/2010 | Cooper | .................. | G11B 27/28 |
| | | | | 382/173 |

(Continued)

FOREIGN PATENT DOCUMENTS

| WO | 2004099763 A1 | 11/2004 |
|---|---|---|
| WO | 2007084378 A3 | 5/2008 |
| WO | 2009111581 A1 | 9/2009 |

OTHER PUBLICATIONS

Pakhomov et al., "Towards a framework for developing semantic relatedness reference standards", Journal of Biomedical Informatics 44 (2011) 251-265. (Year: 2011).*

(Continued)

*Primary Examiner* — Aryan E Weisenfeld
*Assistant Examiner* — Joshua B Blanchette
(74) *Attorney, Agent, or Firm* — Reza Sarbakhsh; Edell, Shapiro & Finnan, LLC

(57) ABSTRACT

The present invention embodiments are directed to methods, systems, and computer programs for identifying relations, within at least one taxonomy, between taxonomy categories and concepts extracted from electronic content. The relations represent semantic similarities for the concepts. The concepts are clustered based on the identified relations within the at least one taxonomy.

12 Claims, 9 Drawing Sheets

(56) References Cited

U.S. PATENT DOCUMENTS

| | | | |
|---|---|---|---|
| 8,266,148 B2* | 9/2012 | Guha | G06F 17/30867 |
| | | | 707/737 |
| 9,690,861 B2* | 6/2017 | Boloor | G06F 17/30867 |
| 2004/0243545 A1* | 12/2004 | Boone | G16H 10/60 |
| 2007/0094188 A1* | 4/2007 | Pandya | G16H 50/20 |
| | | | 706/45 |
| 2008/0201172 A1 | 8/2008 | McNamar | |
| 2008/0201280 A1* | 8/2008 | Martin | G16H 50/20 |
| | | | 706/12 |
| 2009/0037457 A1* | 2/2009 | Musgrove | G06F 16/358 |
| 2009/0106705 A1* | 4/2009 | Takamura | G06F 3/0482 |
| | | | 715/853 |
| 2012/0109641 A1 | 5/2012 | Boone et al. | |
| 2013/0103389 A1 | 4/2013 | Gattani et al. | |
| 2014/0250047 A1 | 9/2014 | Bounouane et al. | |
| 2014/0350961 A1* | 11/2014 | Csurka | G16H 10/60 |
| | | | 705/3 |
| 2015/0356270 A1 | 12/2015 | Devarakonda et al. | |
| 2016/0110447 A1* | 4/2016 | Eckardt | G06F 17/30696 |
| | | | 707/755 |
| 2017/0300636 A1 | 10/2017 | Barker et al. | |

OTHER PUBLICATIONS

T. Pedersen et al. / Journal of Biomedical Informatics 40 (2007) 288-299 (Year: 2007).*

Homayounfar et al; "Data mining research trends in computerized patient records." Proceedings of the Federated Conference on Computer Science and Information Systems (FedCSIS), 2011, pp. 133-139.

Zhang et al; "Medical document clustering using ontology-based term similarity measures." (2008). International Journal of Data Warehousing and Mining, 4(1), Jan.-Mar. 2008, pp. 62-73.

Devarakonda et al.; "Problem-Oriented Patient Record Summary: An Early Report on a Watson Application", 2014, IEEE 16th International Conference on e-Health Networking, Applications and Services (Healthcom), pp. 228-233.

Demner-Fushman et al.; "Answer Extraction, Semantic Clustering, and Extractive Summarization for Clinical Question Answering", Proceedings of the 21st International Conference on Computational Linguistics and 44th Annual Meeting of the ACL, Sydney, Jul. 2006, pp. 841-848.

Resnik; "Semantic Similarity in a Taxonomy: An Information-Based Measure and its Application to Problems of Ambiguity in Natural Language", Journal of Artificial Intelligence Research 11 (1999) 95-130, Jul. 1999, 36 pages.

Shenoy et al.; "A New Similarity Measure for Taxonomy Based on Edge Counting". International Journal of Web & Semantic Technology (IJWesT) vol. 3, No. 4, Oct. 2012, pp. 23-30.

List of IBM Patents or Patent Applications Treated as Related, Jun. 2017, 1 page.

* cited by examiner

|  | CONCEPT A | CONCEPT B | CONCEPT C | CONCEPT D | CONCEPT E |
|---|---|---|---|---|---|
| CONCEPT A | 1 | SIMILARITY (A, B) | SIMILARITY (A, C) | SIMILARITY (A, D) | SIMILARITY (A, E) |
| CONCEPT B | SIMILARITY (A, B) | 1 | SIMILARITY (B, C) | SIMILARITY (B, D) | SIMILARITY (B, E) |
| CONCEPT C | SIMILARITY (A, C) | SIMILARITY (B, C) | 1 | SIMILARITY (C, D) | SIMILARITY (C, E) |
| CONCEPT D | SIMILARITY (A, D) | SIMILARITY (B, D) | SIMILARITY (C, D) | 1 | SIMILARITY (D, E) |
| CONCEPT E | SIMILARITY (A, E) | SIMILARITY (B, E) | SIMILARITY (C, E) | SIMILARITY (D, E) | 1 |

FIG. 7

| PROBLEMS | |
|---|---|
| NAME | DATE |
| ☐ HYPERTENSIVE DISEASE | 12/26/2010 |
| ☐ GASTROESOPHAGEAL REFLUX DISEASE | 12/26/2010 |
| ☐ DIABETES MELLITUS | 12/26/2010 |
| ☐ HYPERLIPIDEMIA | 03/03/2011 |
| ☐ VITAMIN D DEFICIENCY | 06/09/2011 |
| ☐ OBESITY | 12/26/2010 |
| ☐ SLEEP APNEA, OBSTRUCTIVE | 12/26/2010 |
| ☐ ASTHMA | 12/26/2010 |

FIG.8

CLINICALLY RELEVANT MEDICAL CONCEPT CLUSTERING

BACKGROUND

1. Technical Field

Present invention embodiments relate to medical concept clustering, and more specifically, to clinical relevance based medical concept clustering.

2. Discussion of the Related Art

Electronic Medical Records (EMRs) and/or Electronic Health Records (EHRs), collectively and generally referred to herein as EMRs, are electronic records of a patient's health-related information. EMRs are being increasingly adopted in patient care and have the potential to provide substantial benefits to patients, clinicians/physicians, clinic practices, and health care organizations. An EMR may be more beneficial than a paper record because the EMR allows providers to, for example, track data over time, identify patients who are due for preventive visits and screening, monitor how patients measure up to certain parameters (e.g., vaccinations), etc.

SUMMARY

According to one embodiment of the present invention, a method is provided. The method comprises: identifying, within at least one taxonomy, relations between concepts and taxonomy categories extracted from electronic content, wherein the relations represent semantic similarities for the concepts; and clustering the concepts within based on the identified relations within the one or more taxonomies. Embodiments of the present invention further include a system and computer program product for clustering concepts based on identified relations within one or more taxonomies.

BRIEF DESCRIPTION OF THE DRAWINGS

Generally, like reference numerals in the various figures are utilized to designate like components.

FIG. 7 is a table illustrating the content of a similarity matrix in accordance with present invention embodiments;

FIG. 8 is a display of medical conditions that are clustered together in a clinically relevant manner in accordance with present invention embodiments.

DETAILED DESCRIPTION

Electronic Medical Records (EMRs) and/or Electronic Health Records (EHRs), collectively and generally referred to herein as an EMRs, contain a vast amount of clinical data about a patient, such as lists of medical conditions (medical problems), medications, laboratory orders, procedures, etc. Each of these lists may further contain hundreds of entries that are generally ordered alphabetically. The various lists of entries provided in a typical EMR can be difficult for clinicians, who are trained to follow problem-oriented thinking, to mentally process and identify information that is relevant to a particular situation or circumstance.

As such, present invention embodiments are directed to systems, methods, and devices configured to cluster medical concepts (e.g., medical conditions, medications, laboratory orders, procedures, etc.) extracted from an EMR based on clinical relevancy (i.e., group clinically associated concepts together) to facilitate problem-oriented use of EMRs and, in general, reduce a clinician's cognitive load when using EMRs. In particular, the present invention embodiments cluster associated medical concepts of the same semantic group (e.g. disorder or medication) using the concept's distributional semantics extracted from a selected ontology/taxonomy. The present invention embodiments provide for flexible organization of medical concepts which is highly different from the direct use of a specific ontology/taxonomy, which serves a single rigid, pre-defined purpose/view. As described further below, the term "semantic group" can include any grouping of information and is not limited to a Unified Medical Language System (UMLS) defined grouping.

Merely for ease of illustration, the present invention embodiments are described with reference to clustering of medical concepts extracted from electronic content included in an EMR. However, it is to be appreciated that the present invention embodiments may also be used to cluster different types concepts extracted from other electronic content (e.g., a corpora or collection of electronic documents, electronic books, electronic papers, etc.).

Figure 1:
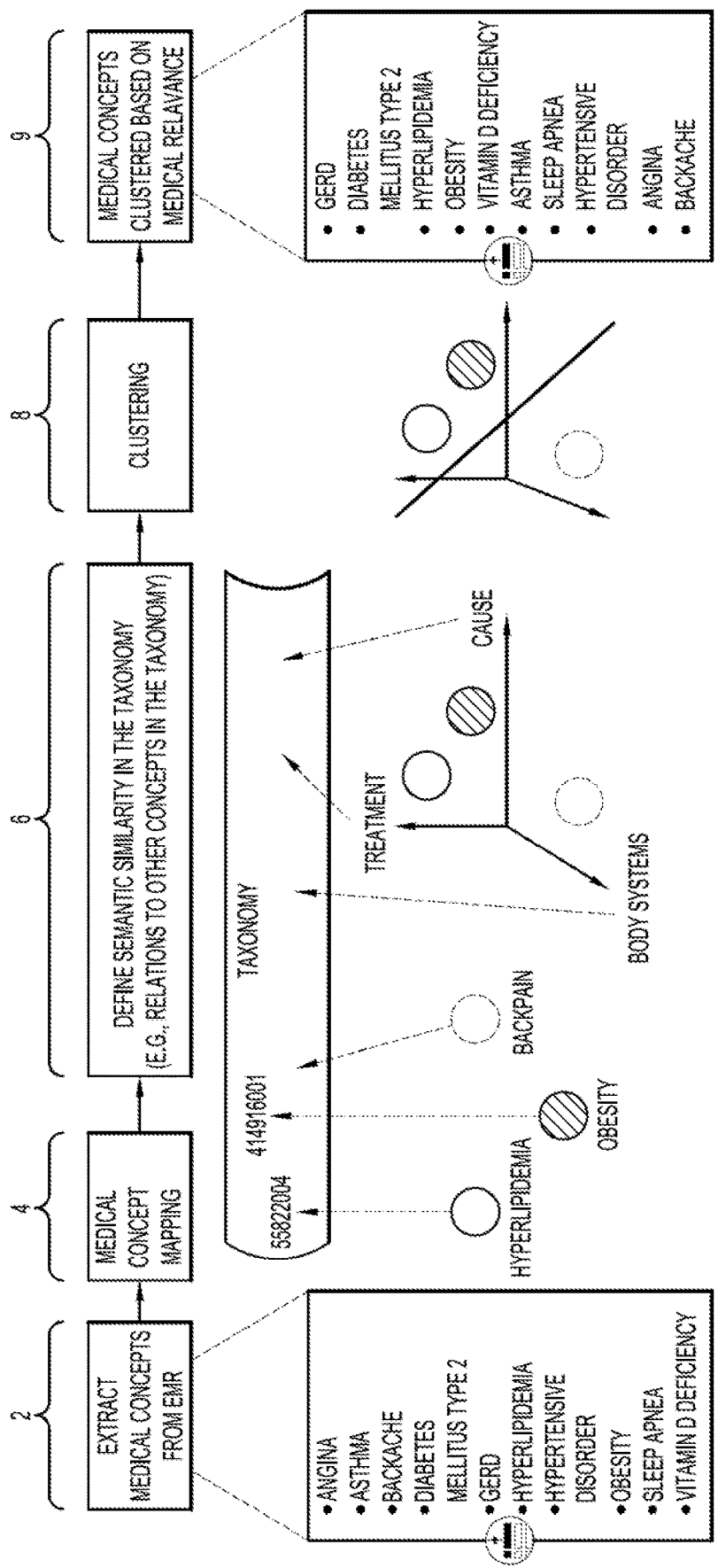
FIG. 1 is a schematic flow diagram of operations in accordance with present invention embodiments.

FIG. 1 is a schematic flow diagram of operations in accordance with present invention embodiments for clinically relevant clustering of medical concepts. The flow of FIG. 1 begins at reference numeral 2 wherein medical concepts are extracted from an EMR. At reference numeral 4, the medical concepts are mapped to one or more taxonomies. At reference numeral 6, schematic similarities in the taxonomy are defined (i.e., relationships between medical concepts are determined). As described further below, similarity between medical concepts is defined in terms of schematic/vector similarity (distances) in a high-dimensional feature space (i.e., in more than 1 dimension, which better matches how human experts think and define similarity/closeness continuously). Entities and relations in any selected taxonomy can be used as features to define the feature space. For example, a feature space can be all concepts in the top "N" levels from a selected taxonomy, and a feature vector of a medical concept can be an array of binary variables indicating whether or not the medical concept is a descendent of the a particular dimension of the feature space. As described further below, the terms "similarity" and/or "distance" include any vector similarity measures (e.g. Euclidean distance, angular, Jaccard index, Ochiai coefficient, etc.).

Referring again to FIG. 1, at reference numeral 8, the schematic similarities between the medical concepts are used to cluster the medical concepts. That is, once the feature space and similarities (distance measures) are defined, medical concepts can then be clustered in a clinically relevant manner using a clustering algorithm. For example, diabetes mellitus (endocrine system), diabetic nephropathy (renal system), obesity, and hyperlipidemia (does not belong to one particular body system) belongs to different body systems and will be classified into different groups, and often will appear scattered in a list if classified and clustered using a fixed taxonomy. This results in a clinically relevant cluster of medical concepts, which is shown in FIG. 1 at reference numeral 9. Each of the operations 2, 4, 6, and 8 of FIG. 1 are described in greater detail below. The above illustrates why a single dimension taxonomic classification can be problematic. It is to be appreciated that the techniques of the present invention embodiments will consider other dimensions beyond the example "body system" and cluster them close to each other.

Figure 2:
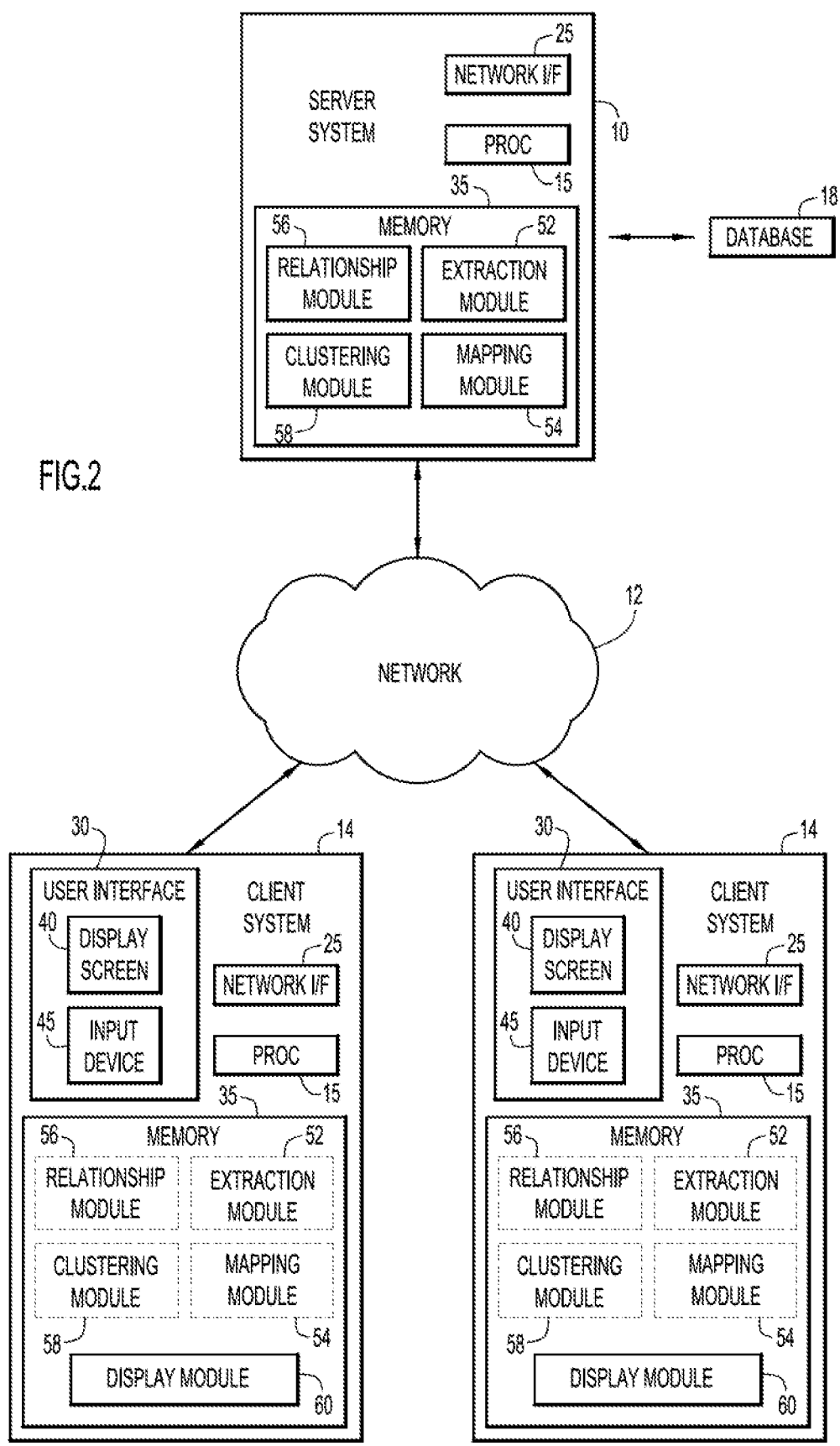
FIG. 2 is a block of an example environment for use with present invention embodiments.

An example environment for use with present invention embodiments is illustrated in FIG. 2. Specifically, the environment includes one or more server systems 10, and one or more client or end-user systems 14. Server systems 10 and client systems 14 may be remote from each other and communicate over a network 12. The network may be implemented by any number of any suitable communications media (e.g., wide area network (WAN), local area network (LAN), Internet, Intranet, etc.). Alternatively, server systems 10 and client systems 14 may be local to each other, and communicate via any appropriate local communication medium (e.g., local area network (LAN), hardwire, wireless link, Intranet, etc.)

Server systems 10 and client systems 14 may be implemented by any conventional or other computer systems preferably equipped with a display or monitor, a base (e.g., including at least one processor 15, one or more memories 35 and/or internal or external network interfaces or communications devices 25 (e.g., modem, network cards, etc.)), optional input devices (e.g., a keyboard, mouse or other input device), and any commercially available and custom software (e.g., server/communications software, module, browser/interface software, etc.). Client systems 14 may also include user interfaces 30 that each includes a display screen 40 and at least one input device 45. Clients 14 and server 10 may also include one or more other interfaces (e.g., command line prompts, menu screens, etc.). The display screens 40 may present a graphical user interface (e.g., GUI, etc.) to solicit information from, or provide information to, users of the client systems 14. The input devices 45 may be, for example, one or more of a keyboard, a mouse, a voice recognition device, etc. allowing a user to enter and/or view information. In certain examples, the display screens 40 and input devices 45 may form an integrated device, such as a touchscreen.

The server system 10 includes an extraction module 52, a mapping module 54, a relationship (similarity) module 56, and a clustering module 58. The extraction module 52 is for extracting medical concepts from the structured and unstructured data in an Electronic Medical Record (EMR). The mapping module 54 is for mapping medical concepts to one or more selected taxonomies and the relationship module 56 is for determining schematic similarities between medical concepts in one or more selected taxonomies. The clustering module 58 is for clustering the medical concepts in a clinically relevant manner based on schematic similarities between the medical concepts.

Also shown in FIG. 2 is a database system 18 that may be configured to store an EMR for analysis in accordance with present invention embodiments. The database system may be implemented by any conventional or other database or storage unit, may be local to or remote from server systems 10 and client systems 14, and may communicate via any appropriate communication medium (e.g., local area network (LAN), wide area network (WAN), Internet, hardwire, wireless link, Intranet, etc.). In other examples, EMRs may be stored at the server system 10.

For ease of illustration, embodiments are described herein with reference to the extraction module 52, the mapping module 54, the relationship module 56, and the clustering module 58 at server system 10. However, it is to be appreciated that the client systems 14 may also or alternatively include one or more of the extraction module 52, the mapping module 54, the relationship module 56, and/or the clustering module 58, which are shown in FIG. 2 within client systems 14 using dashed lines. Client systems 14 also include display modules 60 for displaying clinically relevant clusters of medical concepts at display screens 40.

As noted above, Electronic Medical Records (EMRs) and/or Electronic Health Records (EHRs), collectively and generally referred to herein as an EMRs, contain a vast amount of clinical data about a patient, such as large lists of medical conditions (medical problems), medications, laboratory orders, procedures, etc. However, the lists of entries provided in a typical EMR can be problematic for clinicians trained to follow problem-oriented thinking. As such, presented herein are techniques for clustering medical concepts (e.g., medical conditions, medications, laboratory orders, procedures, etc.) extracted from an EMR into clinically relevant groups so as to reduce a clinician's cognitive load. As used herein, "relevancy" refers to the relative relationships of various medical concepts to high level taxonomy categories and/or sub-categories, collectively and generally referred to herein as "taxonomy categories" or simply "categories" defined for a feature space, rather the absolute location used to cluster the medical concepts.

Further details of aspects of the present invention are described below with reference to clustering of five (5) medical concepts (referred to herein as medical concepts "A," "B," "C," "D," and "E"). It is to be appreciated that reference to five medical concepts (e.g., A, B, C, D, and E) is merely illustrative and that the techniques presented herein may be used to cluster larger numbers of medical concepts.

Figure 3:
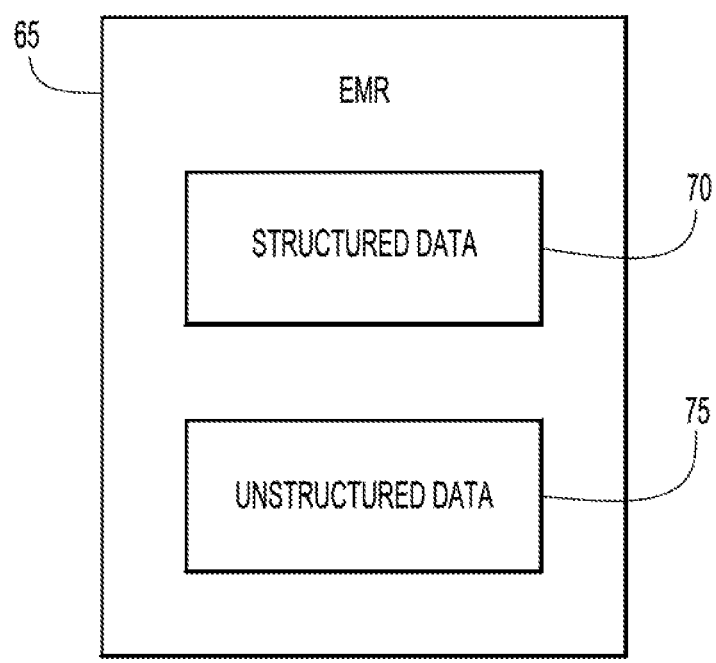
FIG. 3 is a schematic diagram illustrating an EMR for use with present invention embodiments.

In accordance with the techniques presented herein, the medical concepts are extracted from a stored EMR, such as EMR 65 shown in FIG. 3. EMR 65 includes structured data 70 (e.g., a medication list) and unstructured data 75, such as text describing disorders, signs, symptoms, etc. In certain embodiments, "entity linking" or "named-entity recognition and disambiguation," which includes named-entity detection and linking of an entity to a meaning, is used during extraction where a canonical form, for example, a Unified Medical Language System (UMLS) concept, a Systematized Nomenclature of Medicine—Clinical Terms (SNOMED CT) concept, or a Logical Observation Identifiers Names and Codes (LOINC) code is identified for each medical concept.

Current EMR systems (EMRs) contains large amount of unstructured data that is hard to comprehend. Extracting/summarizing this unstructured data can improve the efficiency of current EMRs. For example, unstructured data, such as clinical notes, is useful and important to clinicians, and often contain information missing from structured data. Because unstructured data is harder to comprehend, information extraction and summarization techniques can be applied to generate a dashboard-style summarization. The lists or charts provide a quick view and can link to the detailed evidences/sources. Lists, either from structured data directly, generated from unstructured data, or the combination of the two, can be quite long and unorganized. Accordingly, unstructured data in conventional EMRs is not easily accessible to clinicians. As such, the presence of both structured and unstructured data in an EMR creates a unique computing problem that all data in an EMR cannot be easily clustered and displayed to a clinician in a useable manner. The present invention embodiments are designed to take unstructured data extracted from an EMR and cluster such information along with structured data so that all of the information within an EMR can be readily understood by a clinician (i.e., clustering all medical concepts in a relevant manner). As a result, the present invention embodiments enable a clustered display (at a computing device) that presents greater amounts of EMR information in a more organized manner that is useable by clinicians. The present invention embodiments may be used to cluster a list that is generated from unstructured data, generated from structured data, or generated from both structured data and unstructured data (because the data from both sources is complementary).

Once the medical concepts are extracted from an EMR, the techniques presented herein map the medical concepts to one or more taxonomies. If more than one taxonomy is used, all relationships to all the selected categories are considered simultaneously. For any medical concept that cannot be found in a selected taxonomy, the medical concept will first be mapped to the closest medical concept that can be found in the selected taxonomy. For example, FIGS. 4A and 4B are schematic diagrams illustrating mapping of medical concept A and medical concept C in a first selected taxonomy, referred to herein as Taxonomy 1 (Tax 1).

Figure 4A:
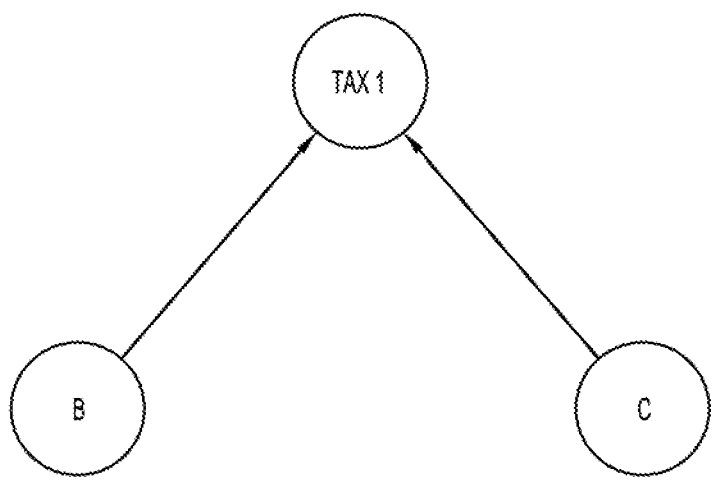
FIGS. 4A and 4B are schematic diagrams illustrating the mapping of medical concepts to a selected taxonomy in accordance with present invention embodiments.
Figure 4B:
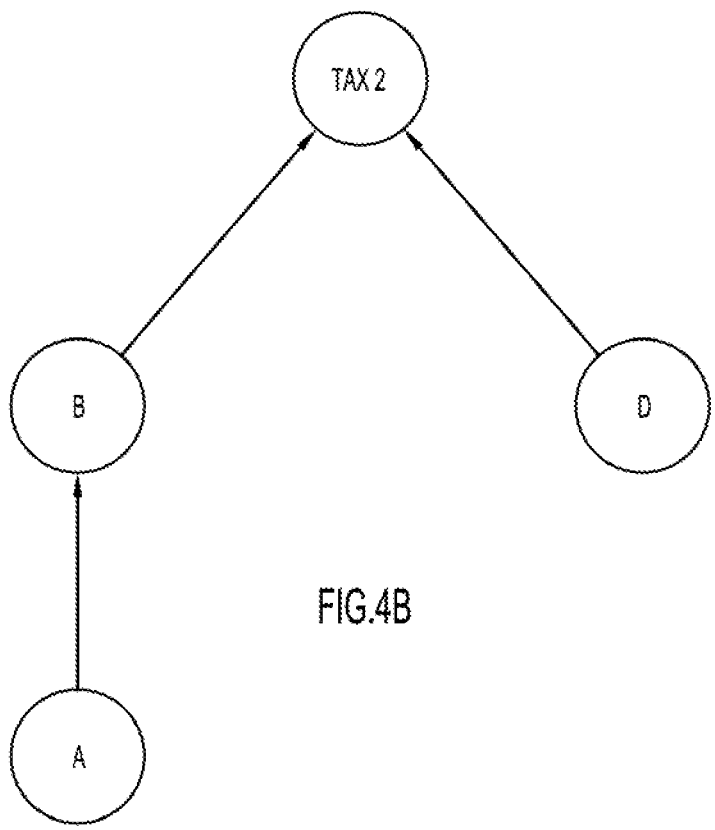

As shown in FIG. 4A, medical concept A is not defined in Tax 1. However, in other taxonomies, such as a second taxonomy referred to herein as Taxonomy 2 (Tax 2), medical concept A is a child of medical concept B, which is a concept that exists in both Tax 1 and Tax 2. Therefore, in order to use Tax 1, medical concept A is first mapped (using Tax 2), to the closet concept that can be found in Tax 1. In other words, medical concepts not found in a selected taxonomy are mapped to that selected taxonomy using relationships identified in one or more other taxonomies (i.e., use other taxonomies to find relationships between the medical concept and one or more medical concepts found within the selected taxonomy). It is to be appreciated that this mapping is not limited to parent-child relationships (e.g., mapping may go sideways to find synonyms). However the search may be depth/hop limited (i.e., if an acceptable fit cannot be found after N hops, then it may be determined that there is no good fit in the taxonomy and no relation for this concept can be found in the given taxonomy).

It is also to be appreciated that there may be limits to the above mapping. For example, there may be circumstances where a medical concept does not fit in the selected taxonomy and, instead of mapping that concept into the selected taxonomy via another taxonomy, the selected taxonomy is interpreted as providing no input to the medical concept.

Figure 5:
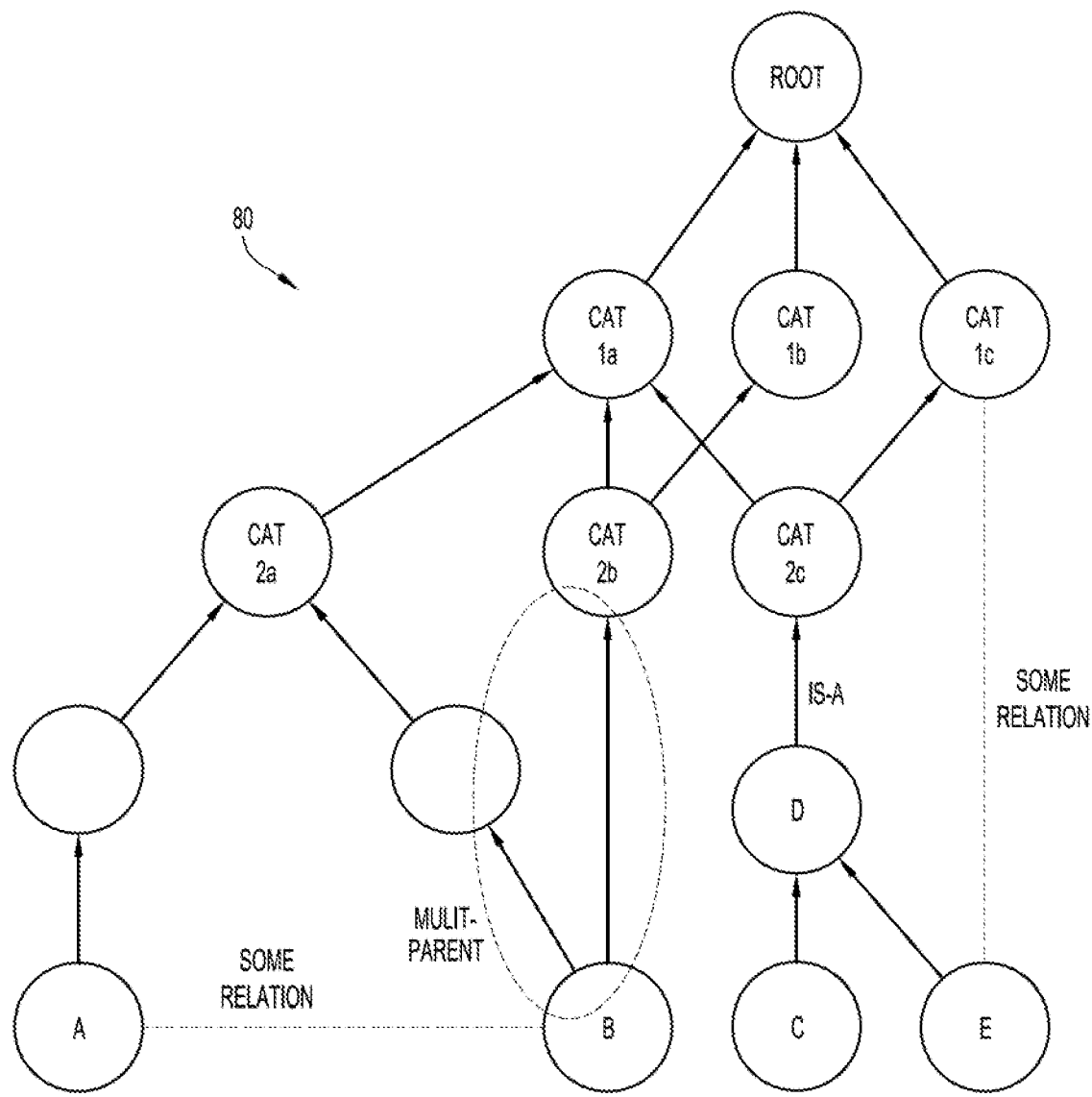
FIG. 5 is a schematic diagram illustrating relationships in a selected taxonomy in accordance with present invention embodiments.

A taxonomy may be, for example, a tree, or an acyclic graph. FIG. 5 illustrates an example acyclic graph 80 where the medical concept B has more than 1 parent. In the present invention embodiments, the medical concepts to be clustered do not need to be at the same level (e.g., medical concept A is 4 levels down from the root, while concept B is 3 or 4 levels down from the root, depending on the path).

The most common type of relationship defined in a taxonomy is the parent-child relationship, or the "is-a" relationship. In the example of FIG. 5, medical concept D is the parent of medical concepts C and E, or, stated differently, "C is a D" and "E is a D." There can be many other types of relationships, for example, "is associated with," "co-occur with," "location of," etc. The present invention embodiments may use any set of relationships, but, as noted above, FIG. 5 uses "is-a" relationships for ease of illustration.

The present invention embodiments define high level categories within a selected taxonomy and use those high level categories as features to construct the feature space. For instance, referring again to FIG. 5, the top 2 levels of categories below the root are chosen to be the feature space. In this example, the determined categories include Category 1a (Cat 1a), Category 1b (Cat 1b), and Category 1c (Cat 1c) that form the first level below the root, as well as Category 2a (Cat 2a), Category 2b (Cat 2b), and Category 2c (Cat 2c) that form the second level below the root. It is to be appreciated that any number of categories can be used (e.g., first level only; first 3 levels; a selected set of categories across multiple levels/regardless of the levels, etc.) in alternative embodiments.

Taxonomies and categories are selected to form the feature space and, therefore, selecting those is effectively defining the meaning of closeness/similarity. In one example, the categories may be based on expert opinions/experiments. For example, one system may utilize the top two levels of selected taxonomies (e.g., MeSH for disorders and NDF-RT for drugs) where the categories are selected based upon previous experiments and expert judgments (e.g., experiments where several combinations were evaluated and the most appropriate were selected based on domain-expert feedback on the result). As such, a user can define the categories based on their own preferences. In another example, categories may be learned. For example, a user can enter examples of what they consider to be similar medical concepts and the system will dynamically learn what categories to select for the clustering. In such examples, the categories may be adapted dynamically based on additional information/feedback provided by a user.

Figure 6:
FIG. 6 is a table illustrating feature values determined for each of a plurality of medical concepts in accordance with present invention embodiments.

After defining the categories that form the feature space, the extracted medical concepts A, B, C, D, and E are used to generate concept vectors, sometimes referred to herein as a "feature values," for the defined feature space. These concepts vectors relate the medical concepts to each of the determined categories. In one embodiment, binary features and an "is-a" relationship limitation is used to define the feature values (concept vectors) between each medical concept and a defined category. In such examples, the feature value is a 1 if a chain of "is-a" relationships can be found linking the target medical concept and the top category, otherwise the value is 0. FIG. 6 is a table 85 illustrating feature values determined for each of the medical concepts A, B, C, D, and E with reference to each of the categories using binary features and an "is-a" relationship limitation. In FIG. 6, the rows represent the feature vector for the respective medical concept (e.g., medical concept A has a feature vector of [1, 0, 0, 1, 0, 0]).

It is to be appreciated that the use of binary features and an "is-a" relationship limitation is illustrative. Alternative embodiments may use other relationship limitations (e.g., "is associated with," "co-occur with," "location of," etc.) in addition to and/or instead of the "is-a" relationship limitation to determine the feature values. Furthermore, instead of binary features, the feature values can represent the property of the actual path, such as the number of hops between a target medical concept and a category, the number of paths that lead from a target concept to a category, etc.

Once the feature values (vectors) are determined, a similarity or distance measure (similarity or distance) between the features values is determined. In one example, the distance between each pair of concept vectors is defined using cosine similarity as shown below in Equation 1.

$$\text{Similarity}(\vec{V_1}, \vec{V_2}) = \cos\theta = \frac{\vec{V_1} \cdot \vec{V_2}}{\|\vec{V_1}\| \|\vec{V_2}\|}, \quad \text{Equation 1}$$

where $\vec{V_1}$ and $\vec{V_2}$ are feature vectors determined for first and second medical concepts, respectively.

It is to be appreciated that other distance measures, such as a pairwise Euclidean distance, Jaccard index, etc. can be used in alternative embodiments. Equation 2, below, illustrates the determination of a pairwise Euclidean distance.

$$\text{Similarity }(\vec{V_1}, \vec{V_2}) = D(\vec{V_1}, \vec{V_2}) = \sqrt{(\vec{V_1} - \vec{V_2}) \cdot (\vec{V_1} - \vec{V_2})}, \quad \text{Equation 2:}$$

where $\vec{V_1}$ and $\vec{V_2}$ are feature vectors determined for first and second medical concepts, respectively.

In certain embodiments, the dimensionality of the feature space is acceptable and no dimensionality reduction is utilized. However, depending on the feature space that is selected, the resulting dimensionality can be quite high and result in a large, but sparse feature space. This may lead to reduced computational performance, over-fitting, and lower accuracy. As such, the present invention embodiments may include dimensionality reduction to optimize the feature space, improve accuracy of clusters, and reduce computer processing time to render a clinically relevant clustered display. Dimensionality reduction may be performed through feature selection (e.g., "sequential backward selection"), where less important features are removed one by one until the desired number of features remain. Alternatively, dimensionality reduction may performed through feature extraction, such as a principal component analysis (PCA) (e.g., unsupervised, linear), a linear discriminant analysis (LDA) (e.g., supervised, linear), Kernel PCA (e.g., unsupervised, nonlinear), etc.

Using the distance/similarity measures defined in the distributional semantics space as described above, the medical concepts are clustered. More specifically, the present invention embodiments generate a similarity matrix for each combination of the medical concepts. FIG. 7 is a table 90 illustrating the content of an example similarity matrix created for combinations of the medical concepts A, B, C, D, and E. Given the similarity matrix (or sometimes a dissimilarity matrix, if instead of similarity of 2 vectors, the dissimilarity measure is defined), a clustering algorithm (e.g., hierarchical clustering algorithm) can be used to cluster the concept vectors. The clustered vectors may then be used to determine a display, such as a display 95 shown in FIG. 8. FIG. 8 illustrates a specific example in which clinically related problems are clustered together. In the example of FIG. 8, the output is a flat list. Depending on the UI/UX preferences and the algorithm used, the output may be hierarchical and can alternatively be presented as a tree or a graph.

Figure 9:
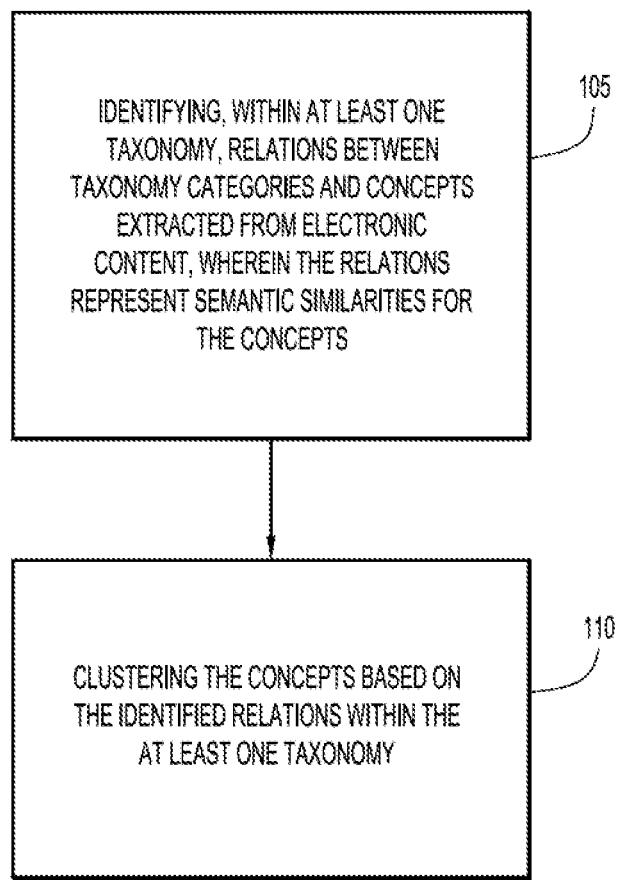
FIG. 9 is a flowchart of a method in accordance with present invention embodiments.

FIG. 9 is a flowchart of a method 100 in accordance with present invention embodiments presented herein. Method 100 begins at 105 where, within at least one taxonomy, relations between taxonomy categories and concepts extracted from electronic content. The relations represent semantic similarities for the concepts. At 110, the concepts are clustered based on the identified relations within the at least one taxonomy.

In summary, present invention embodiments extract concepts (e.g., medical concepts) from structured data (e.g. medication list) and/or from unstructured data (e.g. disorders, signs and symptoms) within electronic content (e.g., content within a patient's electronic medical/health record) and group associated concepts (e.g., clinically associated concepts) together (e.g., to reduce clinicians' cognitive load). The present invention embodiments consider similarity between concepts in more than 1 dimension, which better matches how human experts think and define closeness continuously.

It will be appreciated that the environment described above and illustrated in FIG. 1 represents only a few of the many ways of implementing the present invention embodiments. For example, present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, tablet, PDA, mobile devices, etc.), and may include any commercially available operating system and any combination of commercially available and custom software (e.g., browser software, communications software, server software, profile generation module, profile comparison module, etc.).

It is to be understood that the software (e.g., extraction module 52, a mapping module 54, a relationship (similarity) module 56, and a clustering module 58) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., extraction module 52, a mapping module 54, a relationship (similarity) module 56, and a clustering module 58) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data (e.g. EMRs).

The present invention embodiments may employ any number of any type of user interface (e.g., Graphical User Interface (GUI), command-line, prompt, etc.) for obtaining or providing information, where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer program product for clustering concepts extracted from electronic content, the computer program product comprising one or more non-transitory computer readable storage media collectively having program instructions embodied therewith, the program instructions executable by a processor to cause the processor to:

identify, within a plurality of different taxonomies, relations between taxonomy categories of the different taxonomies and the concepts extracted from the electronic content, wherein the electronic content is from a medical record, the concepts include medical concepts extracted from the medical record, and the plurality of different taxonomies includes medical taxonomies, and wherein the relations represent semantic similarities for the concepts and the identifying relations further includes:

mapping the concepts to each of the plurality of different taxonomies, wherein mapping the concepts includes:

determining a first concept extracted from the electronic content not found in a selected taxonomy of the plurality of different taxonomies;

identifying one or more other taxonomies of the plurality of different taxonomies containing the first concept and determining a second concept that resides in the selected taxonomy and the identified one or more other taxonomies; and mapping the first concept to the second concept within the selected taxonomy when the second concept is closest to the first concept in the identified one or more other taxonomies and within a distance limit of the first concept, wherein the first concept remains unmapped to the selected taxonomy in response to the second concept not satisfying the distance limit;

generating concept vectors relating each of the concepts to one or more corresponding taxonomy categories of the different taxonomies, wherein each concept vector is associated with a concept and includes a plurality of values with each value indicating a relationship between that associated concept and a corresponding taxonomy category, and wherein at least one concept has relations to taxonomy categories in two or more taxonomies; and determining a similarity measure between each of the concept vectors of the concepts based on distances between the concept vectors;

cluster the concepts based on the determined similarity measure between the concept vectors; and generate a visualization of the electronic content with information arranged according to the clustered concepts to identify information within the electronic content relevant to a situation.

2. The computer program product of claim 1, wherein the program instructions further cause the processor to:
perform named-entity recognition and disambiguation on the concepts, which includes concept identification, named-entity detection, and linking of each identified concept to a meaning.

3. The computer program product of claim 1, wherein the program instructions further cause the processor to:
identify the concepts from both structured information and unstructured information within the electronic content.

4. The computer program product of claim 1, wherein the taxonomy categories represent a feature space for clustering of the concepts, and wherein the program instructions further cause the processor to:
perform dimensionality reduction to remove features from the feature space to reduce processing time.

5. A system comprising:
at least one processor configured to:
identify, within a plurality of different taxonomies, relations between taxonomy categories of the different taxonomies and concepts extracted from electronic content, wherein the electronic content is from a medical record, the concepts include medical concepts extracted from the medical record, and the plurality of different taxonomies includes medical taxonomies, and wherein the relations represent semantic similarities for the concepts and the identifying relations further includes:
mapping the concepts to each of the plurality of different taxonomies, wherein mapping the concepts includes:
determining a first concept extracted from the electronic content not found in a selected taxonomy of the plurality of different taxonomies;
identifying one or more other taxonomies of the plurality of different taxonomies containing the first concept and determining a second concept that resides in the selected taxonomy and the identified one or more other taxonomies; and
mapping the first concept to the second concept within the selected taxonomy when the second concept is closest to the first concept in the identified one or more other taxonomies and within a distance limit of the first concept, wherein the first concept remains unmapped to the selected taxonomy in response to the second concept not satisfying the distance limit;
generating concept vectors relating each of the concepts to one or more corresponding taxonomy categories of the different taxonomies, wherein each concept vector is associated with a concept and includes a plurality of values with each value indicating a relationship between that associated concept and a corresponding taxonomy category, and wherein at least one concept has relations to taxonomy categories in two or more taxonomies; and
determining a similarity measure between each of the concept vectors of the concepts based on distances between the concept vectors;
cluster the concepts based on the determined similarity measure between the concept vectors; and
generate a visualization of the electronic content with information arranged according to the clustered concepts to identify information within the electronic content relevant to a situation.

6. The system of claim 5, wherein the at least one processor is further configured to:
identify the concepts from both structured information and unstructured information within the electronic content.

7. The system of claim 5, wherein the at least one processor is further configured to:
perform named-entity recognition and disambiguation on the concepts, which includes concept identification, named-entity detection, and linking of each identified concept to a meaning.

8. The system of claim 5, wherein the taxonomy categories represent a feature space for clustering of the concepts, and wherein the at least one processor is further configured to:
perform dimensionality reduction to remove features from the feature space to reduce processing time.

9. The system of claim 5, wherein the at least one processor is further configured to:
generate a similarity matrix relating the concepts based on the similarity measures; and
cluster the concepts based on the similarity measures.

10. The system of claim 5, wherein the semantic similarities for the concepts represent relative relationships of the concepts to the taxonomy categories such that the concepts are clustered based on identified relevance.

11. The computer program product of claim 1, wherein the program instructions further cause the processor to:
generate a similarity matrix relating the concepts based on the similarity measures; and
cluster the concepts based on the similarity measures.

12. The computer program product of claim 1, wherein the semantic similarities for the concepts represent relative relationships of the concepts to the taxonomy categories such that the concepts are clustered based on identified relevance.

* * * * *